United States Patent [19]

Reagen et al.

[11] Patent Number: 5,382,738

[45] Date of Patent: * Jan. 17, 1995

[54] CHROMIUM COMPOUNDS AND USES IN TRIMERIZATION OR OLIGOMERIZATION

[75] Inventors: William K. Reagen, Stillwater, Minn.; Max P. McDaniel, Bartlesville, Okla.

[73] Assignee: Phillips Petroleum Company, Bartlesville, Okla.

[*] Notice: The portion of the term of this patent subsequent to Feb. 22, 2011 has been disclaimed.

[21] Appl. No.: 194,539

[22] Filed: Feb. 10, 1994

Related U.S. Application Data

[62] Division of Ser. No. 807,299, Dec. 13, 1991.

[51] Int. Cl.$^6$ .................................................. C07C 2/30
[52] U.S. Cl. .................................... 585/512; 502/117; 502/123; 585/522
[58] Field of Search ................ 502/123, 117; 585/522, 585/512

[56] References Cited

U.S. PATENT DOCUMENTS

| | | | |
|---|---|---|---|
| 3,483,269 | 12/1969 | Magoon et al. | 585/522 |
| 4,052,473 | 10/1977 | Yagi et al. | 260/669 P |
| 4,054,612 | 10/1977 | Yagi et al. | 260/669 P |
| 4,310,440 | 1/1982 | Wilson et al. | 252/435 |
| 4,364,855 | 12/1982 | McDaniel et al. | 252/437 |
| 5,043,514 | 8/1991 | McDaniel et al. | 585/522 |
| 5,198,563 | 3/1993 | Reagan et al. | 556/57 |
| 5,288,823 | 2/1994 | Reagan et al. | 526/124 |

OTHER PUBLICATIONS

Rideal, *Concepts in Catalysis*, (1968) (No Month Available), pp. 4–5, Pub. by Academic Press, London & New York.

*Primary Examiner*—Asok Pal
*Attorney, Agent, or Firm*—Lynda S. Jolly

[57] ABSTRACT

Inorganic oxides, modified with a metal alkyl and an unsaturated hydrocarbon, can be used to support a metal source, such as, for example, chromium, and a pyrrole-containing compound. The resultant catalyst system can be used to oligomerize and/or trimerize olefins. Olefin oligomerization and/or trimerization processes are also provided.

20 Claims, No Drawings

CHROMIUM COMPOUNDS AND USES IN TRIMERIZATION OR OLIGOMERIZATION

This application is a division of application Ser. No. 07/807,299, filed Dec. 13, 1991, the entirety of which is herein incorporated by reference.

BACKGROUND OF THE INVENTION

This invention relates to chromium catalysts to oligomerize olefins. This invention also relates to a process to oligomerize olefins.

Supported chromium oxide catalysts have been a dominant factor in the production of olefin polymers, such as polyethylene or copolymers of ethylene and hexene. Supported chromium catalysts can be used in a variety of polymerization processes. Additionally, most known chromium compounds must be supported to be catalytically active and most supported chromium compounds are useful only for olefin polymerization. If an olefin copolymer is desired, the polymerization process becomes more complex, in that two different monomers must be fed to the polymerization reactor.

Olefin trimerization and oligomerization catalysts are also known in the art, but usually lack selectivity to a desired product and have a low product yield. However, olefin trimerization and/or oligomerization, if done efficiently, is a process to provide useful olefins. These olefinic products can be further trimerized, oligomerized and/or, optionally, incorporated into a polymerization process.

SUMMARY OF THE INVENTION

Therefore, it is an object of this invention to provide novel inorganic oxide catalyst supports.

It is another object of this invention to provide a process to prepare inorganic oxide catalyst supports.

It is yet another object of this invention to provide an improved olefin oligomerization catalyst system.

It is still another object of this invention to provide an improved process to oligomerize olefins.

Therefore, in accordance with one embodiment of this invention, an inorganic oxide is treated with a metal alkyl and an unsaturated hydrocarbon to form a novel inorganic oxide catalyst support. In accordance with another embodiment of this invention, the resultant support can be contacted with a chromium source and a pyrrole-containing compound to form a catalyst system. The catalyst system can be used to oligomerize olefins, with high selectivity to a desired olefin product.

DETAILED DESCRIPTION OF THE INVENTION

Supports

Catalyst supports useful in this invention can be any conventional polymerization catalyst support. Preferably, one or more refractory metal inorganic oxides comprise the catalyst support. Exemplary refractory metal inorganic oxide catalyst supports include, but are not limited to, inorganic oxides, either alone or in combination, phosphated inorganic oxides and mixtures thereof. Particularly preferred inorganic oxide supports are selected from the group consisting of silica, silica-alumina, alumina, fluorided alumina, silated alumina, thoria, aluminophosphate, aluminum phosphate, phosphated silica, phosphated alumina, silica-titania, preprecipitated silica/titania, fluorided/silated alumina and mixtures thereof. Furthermore, any one or more of these supports can contain chromium.

The catalyst supports can be prepared in accordance with any method known in the art. Exemplary support method preparations are given in U.S. Pat. Nos. 3,887,494; 3,900,457; 4,053,346; 4,294,724; 4,392,990; 4,405,501; and 4,364,855, hereinafter incorporated by reference. Presently, the most preferred catalyst support, because of the greatest catalytic activity and selectivity, is aluminophosphate, as disclosed in U.S. Pat. No. 4,364,855 (1982).

The metal alkyl can be any heteroleptic or homoleptic metal alkyl compound. One or more metal alkyls can be used. The alkyl ligand(s) on the metal can be aliphatic and/or aromatic. Preferably, the alkyl ligand(s) are any saturated or unsaturated aliphatic radical. The metal alkyl can have any number of carbon atoms. However, due to commercial availability and ease of use, the metal alkyl will usually comprise less than about 70 carbon atoms per metal alkyl molecule and preferably less than about 20 carbon atoms per molecule. Exemplary metal alkyls include, but are not limited to, alkylaluminum compounds, alkylboron compounds, alkylmagnesium compounds, alkylzinc compounds and/or alkyl lithium compounds. Exemplary metal alkyls include, but are not limited to, n-butyl lithium, s-butyllithium, t-butyllithium, diethylmagnesium, diethylzinc, triethylaluminum, trimethylaluminum, triisobutylaluminum, and mixtures thereof.

Preferably, the metal alkyl is selected from the group consisting of non-hydrolyzed, i.e., not pre-contacted with water, alkylaluminum compounds, derivatives of alkylaluminum compounds, halogenated alkylaluminum compounds, and mixtures thereof for improved product selectivity, as well as improved catalyst system reactivity, activity, and/or productivity. Exemplary compounds include, but are not limited to, triethylaluminum, tripropylaluminum, tributylaluminum, diethylaluminum chloride, diethylaluminum bromide, diethylaluminum ethoxide, ethylaluminum sesquichloride, and mixtures thereof for best catalyst system activity and product selectivity. The most preferred alkylaluminum compound is triethylaluminum, for best results in catalyst system activity and product selectivity.

Most preferably, the metal alkyl is a non-hydrolyzed alkylaluminum compound, expressed by the general formulae $AlR_3$, $AlR_2X$, $AlRX_2$, $AlR_2OR$, $AlRXOR$, and/or $Al_2R_3X_3$, wherein R is an alkyl group and X is a halogen atom. Exemplary compounds include, but are not limited to, triethylaluminum, tripropylaluminum, tributylaluminum, diethylaluminumchloride, diethylaluminumbromide, diethylaluminumethoxide, diethylaluminum phenoxide, ethylaluminumethoxy-chloride, and/or ethylaluminum sesquichloride, Preferably, metal alkyl is a trialkylaluminum compound, $AlR_3$, and the most preferred trialkylaluminum compound is triethylaluminum, for reasons given above.

The unsaturated hydrocarbon can be any aromatic or aliphatic hydrocarbon, in a gas, liquid or solid state. Preferably, to effect thorough contacting of the inorganic oxide and metal alkyl, the unsaturated hydrocarbon will be in a liquid state. The unsaturated hydrocarbon can have any number of carbon atoms per molecule. Usually, the unsaturated hydrocarbon will comprise less than about 70 carbon atoms per molecule, and preferably, less than about 20 carbon atoms per molecule, due to commercial availability and ease of use. Exemplary unsaturated, aliphatic hydrocarbon atoms include, but are not limited to, ethylene, 1-hexene, 1,3-butadiene, and mixtures thereof. Exemplary unsaturated, aromatic hydrocarbons include, but are not limited to, toluene, benzene, xylene, mesitylene, hexamethylbenzene, and mixtures thereof. Unsaturated, aromatic hydrocarbons are preferred in order to improve catalyst system stability, as well as produce a highly active catalyst system in terms of activity and selectivity. The most preferred unsaturated aromatic hydrocarbon is toluene, for best resultant catalyst system stability and activity.

The inorganic oxide, metal alkyl, and unsaturated hydrocarbon can be contacted and mixed at any time, temperature and pressure to thoroughly contact the inorganic oxide with the metal alkyl and unsaturated hydrocarbon. For ease of use, ambient temperatures and pressures are preferred. Mixing times can be up to about 24 hours, preferably, less than about 10 hours, and most preferably, from one second to 8 hours. Longer times usually provide no additional benefit and shorter times can be insufficient for thorough contacting.

After the inorganic oxide, metal alkyl, and unsaturated hydrocarbon have been thoroughly contacted, the mixture can be stored until needed for further use. Preferably, the mixture is stored under a dry, inert atmosphere. Optionally, the liquid can be decanted or filtered off and discarded from the inorganic oxide support. The resultant treated, inorganic oxide support can be dried, if desired, and then stored, preferably, under a dry, inert atmosphere until needed for later use.

Catalyst Systems

Catalyst systems prepared in accordance with this invention can be used preferably for olefin oligomerization. Catalyst systems comprise a treated inorganic oxide support, as disclosed earlier, a metal source, and a pyrrole-containing compound. If a solid, treated inorganic oxide support has been separated and recovered from the catalyst support preparation mixture, the catalyst system further comprises a metal alkyl and an unsaturated hydrocarbon compound.

The metal source can be any metal catalytically active to oligomerize olefins. Exemplary metal sources are selected from the group consisting of chromium, nickel, cobalt, iron, molybdenum, and copper. Preferably, catalyst systems comprise a chromium source as the metal source for best resultant catalyst system activity and product selectivity.

If a chromium source is used, the chromium source can be one or more organic or inorganic chromium compounds, wherein the chromium oxidation state is from 0 to 6. As used in this disclosure, chromium metal is included in this definition of a chromium source. Generally, the chromium source will have a formula of $CrX_n$, wherein X can be the same or different and can be any organic or inorganic radical, and n is an integer from 1 to 6. Exemplary organic radicals can have from about 1 to about 20 carbon atoms per radical, and are selected from the group consisting of alkyl, alkoxy, ester, ketone, and/or amido radicals. The organic radicals can be straight-chained or branched, cyclic or acyclic, aromatic or aliphatic, can be made of mixed aliphatic, aromatic, and/or cycloaliphatic groups. Exemplary inorganic radicals include, but are not limited to halides, sulfates, and/or oxides.

Preferably, the chromium source is a chromium(II)- and/or chromium(III)-containing compound which can yield a catalyst system with improved oligomerization activity. Most preferably, the chromium source is a chromium(III) compound because of ease of use, availability, and enhanced catalyst system activity. Exemplary chromium(III) compounds include, but are not limited to, chromium carboxylates, chromium naphthenates, chromium halides, chromium pyrrolides, and/or chromium dionates. Specific exemplary chromium(III) compounds include, but are not limited to, chromium(III) 2,2,6,6-tetramethylheptanedionate [Cr(TMHD)$_3$], chromium(III) 2-ethylhexanoate [Cr(EH)$_3$], chromium(III) naphthenate [Cr(Np)$_3$], chromium(III) chloride, chromium(III) tris(2-ethylhexanoate), chromous bromide, chromic bromide, chromous chloride, chromic chloride, chromous fluoride, chromic fluoride, chromium(III) oxy-2-ethylhexanoate, chromium(III) dichloroethylhexanoate, chromium(III) acetylacetonate, chromium(III) acetate, chromium(III) butyrate, chromium(III) neopentanoate, chromium(III) laurate, chromium(III) stearate, and/or chromium(III) oxalate.

Specific exemplary chromium(II) compounds include, but are not limited to, chromium(II) bis(2-ethylhexanoate), chromium(II) acetate, chromium(II) butyrate, chromium(II) neopentanoate, chromium(II) laurate, chromium(II) stearate, chromium(II) oxalate and/or chromium(II) pyrrolides.

The pyrrole-containing compound can be any pyrrole-containing compound that will react with a chromium source to form a chromium pyrrolide complex. As used in this disclosure, the term "pyrrole-containing compound" refers to hydrogen pyrrolide, i.e., pyrrole, ($C_4H_5N$), derivatives of hydrogen pyrrolide, as well as metal pyrrolide complexes. A "pyrrolide" is defined as a compound comprising a 5-membered, nitrogen-containing heterocycle, such as, for example, pyrrole, derivatives of pyrrole, and mixtures thereof. Broadly, the pyrrole-containing compound can be pyrrole and/or any heteroleptic or homoleptic metal complex or salt, containing a pyrrolide radical, or ligand. The pyrrole-containing compound can be either affirmatively added to the reaction, or generated in-situ.

Generally, the pyrrole-containing compound will have from about 1 to about 20 carbon atoms per molecule. Exemplary pyrrolides are selected from the group consisting of hydrogen pyrrolide (pyrrole), lithium pyrrolide, sodium pyrrolide, potassium pyrrolide, cesium pyrrolide, and/or the salts of substituted pyrrolides, because of high reactivity and activity with the other reactants. Examples of substituted pyrrolides include, but are not limited to, pyrrole-2-carboxylic acid, 2-acetylpyrrole, pyrrole-2-carboxaldehyde, tetrahydroindole, 2,5-dimethylpyrrole, 2,4-dimethyl-3-ethylpyrrole, 3-acetyl-2,4-dimethylpyrrole, ethyl-2,4-dimethyl-5-(ethoxycarbonyl)-3-pyrrolepropionate, ethyl-3,5-dimethyl-2-pyrrolecarboxylate. When the pyrrole-containing compound contains chromium, the resultant chromium compound can be called a chromium pyrrolide.

The most preferred pyrrole-containing compound used in a oligomerization catalyst system, prepared in accordance with this invention, are selected from the group consisting of hydrogen pyrrolide, i.e., pyrrole ($C_4H_5N$) and/or 2,5-dimethylpyrrole. While all pyrrole-containing compounds can produce catalyst systems with high activity and productivity, use of pyrrole and/or 2,5-dimethylpyrrole can produce a catalyst system with enhanced activity and selectivity to a desired oligomerized product, such as, for example, the oligomerization of ethylene to 1-hexene, as well as decreased polymer, i.e., solids, production.

Optionally, and preferably, a halide source is also present in the reaction mixture comprising a treated inorganic oxide support, a chromium source and a pyrrole-containing compound. The presence of a halide source in the reaction mixture can increase catalyst system activity and productivity, as well as increase product selectivity. Exemplary halides include, but are not limited to fluoride, chloride, bromide, and/or iodide. Due to ease of use and availability, chloride is the preferred halide. Based on improved activity, productivity, and/or selectivity, bromide is the most preferred halide.

The halide source can be any compound containing a halogen. Exemplary compounds include, but are not limited to, compounds with a general formula of $R_mX_n$, wherein R can be any organic and/or inorganic radical, X can be a halide, selected from the group consisting of fluoride, chloride, bromide, and/or iodide, and $m+n$ can be any number greater than 0. If R is an organic radical, preferably R has from about 1 to about 70 carbon atoms per radical and, most preferably from 1 to 20 carbon atoms per radical, for best compatibility and catalyst system activity. If R is an inorganic radical, preferably R is selected from the group consisting of aluminum, silicon, germanium, hydrogen, boron, lithium, tin, gallium, indium, lead, and mixtures thereof. Specific exemplary compounds include, but are not limited to, methylene chloride, chloroform, benzylchloride, silicon tetrachloride, tin(II) chloride, tin(IV) chloride, germanium tetrachloride, boron trichloride, aluminum tribromide, aluminum trichloride, 1,4-di-bromobutane, and/or 1-bromobutane. Most preferably, the halide source is selected from the group consisting of tin (IV) halides, germanium halides, and mixtures thereof.

Furthermore, the chromium source, the metal alkyl and/or unsaturated hydrocarbon can contain and provide a halide to the reaction mixture. Preferably, the halide source is an alkylaluminum halide and is used in conjunction with alkylaluminum compounds due to ease of use and compatibility, as well as improved catalyst system activity and product selectivity. Exemplary alkylaluminum halides include, but are not limited to, diisobutylaluminum chloride, diethylaluminum chloride, ethylaluminum sesquichloride, ethylaluminum dichloride, diethylaluminum bromide, diethylaluminum iodide, and mixtures thereof.

The amount of each reactant used to prepare an oligomerization catalyst system can be any amount sufficient that, when combined with one or more olefins, oligomerization, as defined in this disclosure, occurs.

As disclosed earlier, if a dried, treated inorganic oxide support is combined with a metal source and a pyrrole-containing compound, preferably a metal alkyl and an unsaturated hydrocarbon are also re-contacted with the catalyst system. The metal alkyl and unsaturated hydrocarbon can be any metal alkyl and unsaturated hydrocarbon, as disclosed earlier.

The catalyst system components can be combined in any manner under conditions suitable to form an effective catalyst system and can be prepared either external to a oligomerization reactor, or in-situ in a oligomerization reactor. The reaction preferably occurs in the absence of oxygen, which can deactivate the catalyst, and under anhydrous conditions, i.e., in the initial absence of water. Therefore a dry, inert atmosphere, such as, for example, nitrogen and/or argon is most preferred.

When an oligomerization catalyst system is prepared prior to addition to an oligomerization reactor, a solid catalyst system can be recovered according to any method known in the art. Recovery of a solid catalyst system can help reduce, or eliminate, the presence of any unsaturated hydrocarbon(s), which are not oligomerization reactants, can be oligomerization reaction poisons. For example, aromatic hydrocarbons, such as, for example, excess toluene, can poison a oligomerization reaction.

Preferably, a solid catalyst system is recovered by filtration and subsequently washed with a sufficient amount of a saturated hydrocarbon. Saturated hydrocarbons useful for washing include, but are not limited to, aliphatic hydrocarbons having from about 1 to about 2 carbon atoms per molecule. Preferably, that aliphatic hydrocarbon is a linear aliphatic hydrocarbon and has from 1 to 15 carbon atoms per molecule. Exemplary saturated hydrocarbons include, but are not limited to, methane, propane, butane, pentane, hexane, octane, and/or 1-decane.

Preferably, the oligomerization catalyst system is washed with a saturated hydrocarbon wash solution until a clear filtrate is observed. After washing, the solid catalyst system can be stored under a dry, inert atmosphere until ready for use. The washed, solid catalyst system can then be feed directly to an oligomerization reactor. In a second embodiment, the catalyst system can be prepared in-situ, directly in an oligomerization reactor. A chromium source, pyrrole-containing compound, the dried treated support, and a metal alkyl can be charged directly to the oligomerization reactor. The presence of an unsaturated hydrocarbon is provided by one or more of the oligomerization reactants in the reactor. The pressure and temperature of the reactor, both before and during an oligomerization reaction, are suitable to form an effective catalyst system.

The reaction pressure, during catalyst system preparation, can be any pressure which does not adversely effect the reaction. Generally, pressures within the range of from about atmospheric pressure to about three atmospheres are acceptable. For ease of operation atmospheric pressure is generally employed.

The reaction temperature, during catalyst system preparation, can be any temperature. In order to effectuate a more efficient reaction, temperatures which maintain the reaction mixture in a liquid state, for reasons given above, are preferred.

The reaction time, during catalyst system preparation, can be any amount of time necessary for the reaction to occur. The reaction can be considered a dissolution process; any amount of time wherein substantially all soluble reactants can be dissolved is sufficient. Depending on the reactants, as well as the reaction temperature and pressure, reaction time can vary. Times of less than about 1 day can be sufficient. Usually, reaction time is less than about 60 minutes. Under optimum conditions, the reaction time can be within the range of from about 1 second to about 15 minutes. Longer times usually provide no additional benefit and shorter times may not allow sufficient time for complete reaction.

Reactants

Oligomerization, as used in this disclosure, is defined as the combination of any two, three, or more olefins. For example, oligomerization can be a reaction wherein the number of olefin i.e., carbon-carbon double bonds is reduced by two. Reactants applicable for use in the oligomerization process of this invention are olefinic compounds which can a) self-react, i.e., oligomerize, to give useful products such as, for example, the self reaction of ethylene can give one hexene and the self-reaction of 1,3-butadiene can give 1,5-cyclooctadiene; and/or b) olefinic compounds which can react with other olefinic compounds, i.e., to give useful products such as, for example, co-oligomerize of ethylene plus hexene can give one decene and/or 1-tetradecene, co-oligomerize of ethylene and 1-butene gives one octene, co-oligomerize of 1-decene and ethylene can give 1-tetradecene and/or 1-docosene, or co-oligomerize of 1,3-butadiene and 1,5-hexadiene can give 1,5-cyclo-decadiene. For example, the number of olefin bonds in the combination of three ethylene units is reduced by two, to one olefin bond, in 1-hexene. In another example, the number of olefin bonds in the combination of two 1,3-butadiene units, is reduced by two, to two olefin bonds in 1,5-cyclooctadiene. As used herein, the term "oligomerization", is intended to include dimerization of diolefins, as well as "co-oligomerization", both as defined above.

Suitable oligomerizable olefin compounds are those compounds having from about 2 to about 30 carbon atoms per molecule and having at least one olefinic double bond. Exemplary mono-1-olefin compounds include, but are not limited to acyclic and cyclic olefins such as, for example, ethylene, propylene, 1-butene, 2-butene, isobutylene, 1-pentene, 2-pentene, 1-hexene, 2-hexene, 3-hexene, 1-heptene, 2-heptene, 3-heptene, the four normal octenes, the four normal nonenes, and mixtures of any two or more thereof. Exemplary diolefin compounds include, but are not limited to, 1,3-butadiene, 1,4-pentadiene, and 1,5-hexadiene. If branched and/or cyclic olefins are used as reactants, while not wishing to be bound by theory, it is believed that steric hindrance could hinder the oligomerization process. Therefore, the branched and/or cyclic portion(s) of the olefin preferably should be distant from the carbon-carbon double bond.

Catalyst systems produced in accordance with this invention preferably are employed as oligomerization catalyst systems.

Reaction Conditions

The reaction products, i.e., olefin dimers trimers and oligomers as defined in this specification, can be prepared from the catalyst systems of this invention by solution reactions, slurry reactions, and/or gas phase reaction techniques using conventional equipment and contacting processes. Contacting of the monomer or monomers with a catalyst system can be effected by any manner known in the art of solid catalysts. One convenient method is to suspend the catalyst system in an organic medium and to agitate the mixture to maintain the catalyst system in suspension throughout the trimerization process. Other known contacting methods, such as, for example, fluidized bed, gravitating bed, and fixed bed, can also be employed.

Reaction temperatures and pressures can be any temperature and pressure which can oligomerize the olefin reactants. Generally, reaction temperatures are within a range of about 0° to about 250° C. Preferably, reaction temperatures within a range of about 60° to about 200° C. and most preferably, within a range of 80° to 150° C. are employed. Generally, reaction pressures are within a range of about atmospheric to about 2500 psig. Preferably, reaction pressures within a range of about atmospheric to about 1000 psig and most preferably, within a range of 300 to 700 psig are employed.

Too low of a reaction temperature can produce too much undesirable insoluble product and too high of a temperature can cause decomposition of the catalyst system and reaction products. Too low of a reaction pressure can result in low catalyst system activity. Too high of a pressure can cause production of too much undesirable insoluble product.

Optionally, hydrogen can be added to the reactor to accelerate the reaction and/or increase catalyst system activity.

Catalyst systems of this invention are particularly suitable for use in oligomerization processes. The slurry process is generally carried out in an inert diluent (medium), such as a paraffin, cycloparaffin, or aromatic hydrocarbon. Exemplary reactor diluents include, but are not limited to, isobutane and cyclohexane. Isobutane can decrease the swelling of the polymer product and enhance heterogeneous catalyst activity. However, a homogenous oligomerization catalyst system is more soluble in cyclohexane. Therefore, a preferred diluent for a homogeneous catalyzed oligomerization process is cyclohexane. When the reactant is predominately ethylene, a temperature in the range of about 0° to about 300° C. generally can be used. Preferably, when the reactant is predominately ethylene, a temperature in the range of about 60° to about 110° C. is employed.

Products

The olefinic products of this invention have established utility in a wide variety of applications, such as, for example, as monomers for use in the preparation of homopolymers, copolymers, and/or terpolymers.

The further understanding of the present invention and its advantages will be provided by reference to the following examples.

EXAMPLES

Example I

In the following Runs, all catalyst systems were prepared in a glove-box, under dry nitrogen at ambient temperature and pressure. The catalyst support was weighed into a glass vial. Catalyst supports were aluminophosphate supports, prepared in accordance with U.S. Pat. No. 4,364,855, activated at 700° C., with a P/Al molar ratio of 0.4 or 0.9. Runs 101–111, 118–120 and 125 had a support P/Al molar ratio of 0.4. Runs 112–117 and 121–124 had a support P/Al molar ratio of 0.9. Then, toluene and a solution of triethylaluminum (TEA) in toluene were added to the support. The support, TEA, and toluene slurry was shaken for about 24 hours in all Runs, except Runs 114–117 and 121–125, which were shaken for about 4 days. Thus, all supports in Example I were treated with metal alkyl (TEA) and an unsaturated hydrocarbon (toluene), prior to contacting a chromium source.

Then chromium pyrrolide.dimethoxyethane ([Na(DME)$_2$][Cr(C$_4$H$_4$N)$_3$Cl.DME]), (Cr(Py)$_3$DME) was added to the support slurry and shaken again at ambient temperature and pressure. Runs 101–103, were shaken for 6 days; Runs 104–113 and 118–120 were shaken for 24 hours; Runs 114–117 and 121 were shaken for 4 days. A brown slurry was produced.

Excess liquid was decanted, the remaining solids were washed with cyclohexane until a clear wash solution was observed. The solids were vacuum dried at ambient temperature (about 20° C.) and stored under dry nitrogen until use.

All oligomerization Runs were carried out in a two liter reactor under slurry (particle form) conditions. The diluent was isobutane and the reactor temperature was 90° C., except Runs 113, 115 and 118 where the reactor temperature was 70° C.; Runs 113 where the reactor temperature was 110° C.; and Run 117 where the reactor temperature was 100° C. Reactor pressure held at 550 psig during the oligomerization, with ethylene being fed on demand.

The actual charging of the reactor was accomplished by the following method. After purging the reactor at 100° C. with a stream of nitrogen for at least 15 minutes, the reactor temperature was lowered to 90° C., unless otherwise indicated, and a preweighed amount of supported chromium pyrrolide catalyst system, unless otherwise indicated, was charged against a slight countercurrent of nitrogen. One liter of isobutane was then charged to the reactor and finally the reactor pressurized with ethylene.

The ethylene consumed was determined using a precalibrated ethylene flow meter. Samples of the liquid product mixture were taken after a 30 minute run time, without depressurizing the reactor by filling to 220-300 psig a steel sampling cylinder adapted to the reactor with a dip tube fitted with a fritted tip extending into the bottom of the reactor vessel. Samples were analyzed by gas chromatography and gas chromatography-mass spectrometry. Selectivities were normalized to 100%. Solid products were obtained by venting the reactor to atmosphere and decanting the liquids from the solid material. The solids were then dried at 100° C. in a vacuum oven and weighed. The yield of solid product was obtained by weighing the combined solid and catalyst residues and subtracting from this the preweighed catalyst charge. The yield of volatile products was obtained by subtracting the yield of solid products from the grams of ethylene consumed as recorded by the flow meter.

Activity typically ranged from 300-1500 g product/g catalyst/hour calculated for 30 minute run time, as shown in Table I. The product obtained typically was represented by 97-99.5% by weight liquids and 0.5-3% by weight polymer (wax). The liquid fraction was typically 85% hexenes, 11% decenes, 2% tetradecences, based on the total weight of the liquid fraction. The balance of the liquid product mixture was a trace level distribution of olefins typically totaling about 1-2% by weight of the product mixture.

TABLE I

| Run | Amount TEA added to Reactor | Grams Cr Cmpd. Used | Grams Catalyst Charged | Productivity, g prod./g Cat./hr | Total Grams Prod.[a] | Weight Percent Solid[a] | Weight Percent Liquid | Observations |
|---|---|---|---|---|---|---|---|---|
| 101 | 1.5 ml, 1.3% | 0.110 | 0.3326 | 1190 | 207 | 2 | 98 | — |
| 102 | 2.5 ml, 1.3% | 0.110 | 0.2106 | 900 | 95 | 3 | 97 | — |
| 103 | 1.8 ml, 1.3% | 0.110 | 0.2964 | 915 | 137 | 3 | 97 | — |
| 104 | 1.5 ml, 1.3% | 0.210 | 0.4706 | 1150 | 271 | 2 | 98 | — |
| 105 | 1.5 ml, 1.3% | 0.210 | 0.0564 | no activity | — | — | — | small amount tan powder |
| 106 | 1.5 ml, 1.3% | 0.210 | 0.3878 | 1300 | 271 | 1 | 99 | — |
| 107 | 1.5 ml, 1.3% | 0.210 | 0.1345 | no activity | — | — | — | small amount brown powder; smell of ether |
| 108 | 1.5 ml, 1.3% | 0.210 | 0.1577 | 2560[b] | 116 | 2 | 98 | — |
| 109 | 0 | 0.210 | 0.1895 | 1650 | 142 | <1 | >99 | — |
| 110 | 1.5 ml, 0.5% | 0.326 | 0.3126 | 810 | 128 | 2 | 98 | — |
| 111 | 1.5 ml, 0.5% | 0.210 | 0.5314 | 770 | 204 | 2 | 98 | — |
| 112 | 1.5 ml, 0.5% | 0.210 | 0.1836 | 530 | 49 | 2 | 98 | — |
| 113 | 0 | 0.210 | 0.3208 | 440 | 71 | 1 | 99 | — |
| 114 | 1.5 ml, 0.5% | 2.25 | 0.3555 | 910 | 161 | 1 | 99 | waxy solids |
| 115 | 1.5 ml, 0.5% | 2.25 | 0.1354 | 1550 | 106 | 1 | 99 | — |
| 116 | 1.5 ml, 0.5% | 2.25 | 0.1574 | 1550 | 122 | 1 | 99 | — |
| 117 | 1.5 ml, 0.5% | 2.25 | 0.1693 | 1170 | 98 | 1 | 99 | — |
| 118 | 1.5 ml, 0.5% | 0.225 | 0.2034 | 1180 | 120 | <1 | >99 | — |
| 119 | 1.5 ml, 0.5% | 0.225 | 0.2961 | 1070 | 158 | <1 | >99 | — |
| 120 | 1.5 ml, 0.5% | 0.225 | 0.3357 | 620 | 104 | 2 | 98 | — |
| 121 | 1.0 ml, 1.0% | 2.25 | 0.3801 | 840 | 159 | 3 | 97 | — |
| 122 | 1.0 ml, 1.0% | 2.25 | 0.0392 | 1960 | 247 | 3 | 97 | — |
| 123 | 1.0 ml, 1.0% | 2.20 | 0.3879 | 1000 | 194 | 4 | 96 | 700 psig in reactor; 30 psig $H_2$ added before ethylene |
| 124 | 0 | 2.20 | 0.2419 | 1040 | 129 | 2 | 98 | added 30 psig $H_2$ after 15 minutes |
| 125 | 1.5 ml, 1.0% | 2.23 | 0.5500 | 630 | 173 | 3 | 97 | cyclohexane diluent, not iso-butane |

[a]Including residual catalyst system.
[b]15 minute run time

The data in Table I show that catalyst systems prepared with a support pre-treated with a metal alkyl and an unsaturated hydrocarbon produce a small amount of polymer (wax) and a high quantity of liquid olefins.

Example II

In the following Runs, all catalyst systems were prepared in a glove-box, under dry nitrogen at ambient temperature and pressure. The catalyst support was weighed into a glass vial. Catalyst supports were either aluminophosphate supports, prepared in accordance with U.S. Pat. No. 4,364,855, activated at 700° C., with P/Al molar ratio of 0.4 or 0.9; alumina ($Al_2O_3$), commercially available from Akzo Chemie America, as Ketjen B, activated at 600° C. The support in Run 201 was alumina. Run 206-207, 211 and 212 had a support P/Al molar ratio of 0.4. Runs 207-210 had a support P/Al molar ratio of 0.9. Then, a chromium source and optionally TEA and/or toluene were added to the support. Thus, none of the supports in Example II were treated with a metal alkyl and/or an unsaturated hydrocarbon prior to contacting a chromium source. The chromium sources given in Table II are chromium pyrrolide.dimethoxyethane ([Na(DME)$_2$][Cr(C$_4$H$_4$N)$_3$Cl.DME]), (Cr(Py)$_3$DME); cyclopentadienyl chromium (Cr(C$_5$H$_5$)$_2$), (CrCp$_2$); and bis-benzene chromium (Cr(C$_6$H$_6$)$_2$), (Cr(Ben)$_2$). Runs 203–206, 211 and 212 did not have triethylaluminum (TEA) added to the vial. Runs 207–210 did not have additional toluene added to the vial. The slurry was shaken for about 24 hours in all Runs except Runs 203–204, which were shaken for about 30 minutes.

Excess liquid was decanted, the remaining solids were washed with cyclohexane until a clear wash solution was observed. The solids were dried under vacuum at ambient temperature (about 20° C.) and stored under dry nitrogen until used.

All oligomerization runs were carried out in a 2 liter reactor under slurry (particle form) conditions. The diluent was isobutane and the reactor temperature was 90° C., except Run 207 where the reactor temperature was 70° C., Run 208 where the reactor temperature was 80° C., Run 209 where the reactor temperature was 100° C., and Run 210 where the reactor temperature was 110° C. Reactor pressure was held at 550 psig during the oligomerization with ethylene being fed on demand.

The reactor was charged as described in Example I. Ethylene consumption and product analyses were done as described in Example I.

The results of the oligomerization Runs are given in Table II.

limited thereby but is intended to cover all changes and modifications within the spirit and scope thereof.

That which is claimed is:

1. A process to oligomerize olefins with a catalyst composition comprising:
   a) a metal source which is a chromium compound and
   b) a pyrrolide compound;
   wherein said metal source and said pyrrolide compound are supported on a modified inorganic oxide composition which comprises an inorganic oxide; a metal alkyl selected from the group consisting of alkyl aluminum compounds, alkyl boron compounds, alkyl magnesium compounds, alkyl zinc compounds, alkyl lithium compounds, and mixtures of two or more thereof; and an unsaturated hydrocarbon.

2. A process according to claim 1 wherein said inorganic oxide is selected from the group consisting of silica, silica-alumina, alumina, fluorided alumina, silated alumina, thoria, aluminophosphate, aluminum phosphate, phosphated silica, phosphated alumina, silica-titania, coprecipitated silica/titania, fluorided/silated alumina, and mixtures thereof.

3. A process according to claim 2 wherein said inorganic oxide is aluminophosphate.

4. A process according to claim 1 wherein said metal alkyl is a alkyl aluminum compound.

5. A process according to claim 4 wherein said alkyl aluminum compound is triethyl aluminum.

6. A process according to claim 1 wherein said unsaturated hydrocarbon is an aromatic hydrocarbon having less than about 70 carbon atoms per molecule.

7. A process according to claim 1 wherein said pyrrolide compound is selected from the group consisting of

TABLE II

| Run | Amount TEA Added[a] to Reactor | TEA Used in Catalyst Prep | Cr Cmpd | Grms Cr Cmpd Used | Grms Catalyst Charged | Productivity, g prod./g cat./hr. | Total Grms Prod. | Wt. % Solid | Wt. % Liquid | Observations |
|---|---|---|---|---|---|---|---|---|---|---|
| 201 | 1.5 ml, 1.3% | yes | CrPy$_3$DME | 0.10 | 0.2216 | 460 | 51 | 2 | 98 | — |
| 202 | 1.5 ml, 0.5% | yes | CrPy$_3$DME | 0.2259 | 0.6213 | 440 | 136 | <1 | >99 | waxy solids |
| 203 | 0.5 ml, 0.5% | no | CrCp$_2$ | 0.10 | 0.1403 | 510 | 24 | 83 | 17 | — |
| 204 | 0.5 ml, 0.5% | no | Cr(Ben)$_2$ | 0.10 | 0.2629 | 770 | 101 | 75 | 25 | solid polymer appears wet; heavy odor of olefins |
| 205 | 0 | no | Cr(Ben)$_2$ | 0.10 | 0.1834 | 630 | 58 | 79 | 21 | polymer had olefin odor |
| 206 | 1.5 ml, 0.5% | no | Cr(Ben)$_2$ | 0.10 | 0.5441 | 1050 | 287 | >99 | <1 | solid polymer appears wet; olefin odor |
| 207 | 1.5 ml, 0.5% | yes | CrPy$_3$DME | 0.10 | 0.3532 | 2550 | 180 | 2 | 98 | — |
| 208 | 1.5 ml, 0.5% | yes | CrPy$_3$DME | 0.10 | 0.1329 | 1930 | 118 | 17 | 83 | — |
| 209 | 1.5 ml, 0.5% | yes | CrPy$_3$DME | 0.10 | 0.0745 | 2950 | 110 | 1 | 99 | low catalyst charge |
| 210 | 1.5 ml, 0.5% | yes | CrPy$_3$DME | 0.10 | 0.0912 | 2390 | 109 | 1 | 99 | — |
| 211 | 0.5 ml, 1.0% | no | Cr(Ben)$_2$ | 0.978 | 0.3571 | 1240 | 222 | 86 | 14 | — |
| 212 | 0.5 ml, 1.0% | no | CrCp$_2$ | 0.914 | 0.6043 | 170 | 35 | >99 | <1 | polymer damp; smelled of olefins |

Comparison of the data in Table II with the data in Table I shows that pre-treatment of a support with a metal alkyl and an unsaturated hydrocarbon consistently results in low polymer and high liquid production. The data in Table II also show that the presence of a pyrrole-containing compound can improve the percentage product yield of liquids.

While this invention has been described in detail for the purpose of illustration, it is not to be construed as pyrrole, derivatives of pyrrole, alkali metal pyrrolides, salts of alkali metal pyrrolides, and mixtures thereof.

8. A process according to claim 7 wherein said pyrrolide compound is selected from the group consisting of pyrrole, 2,5-dimethylpyrrole, and mixtures thereof.

9. A process according to claim 1 wherein said olefin has from about 2 to about 30 carbon atoms per molecule.

10. A process according to claim 9 wherein said olefin is ethylene.

11. A process according to claim 1 wherein said oligomerization is carried out at a temperature within a range of about 0° to about 250° C. and a pressure within a range of about atmospheric to about 2500 psig.

12. A process to oligomerize ethylene to 1-hexene with a composition comprising:
   a) a metal source which is a chromium compound and
   b) a pyrrolide compound;
   c) wherein said metal source and said pyrrolide compound are supported on a modified inorganic oxide composition which comprises an inorganic oxide; a metal alkyl selected from the group consisting of alkyl aluminum compounds, alkyl boron compounds, alkyl magnesium compounds, alkyl zinc compounds, alkyl lithium compounds, and mixtures of two or more thereof; and an unsaturated hydrocarbon.

13. A process according to claim 12 wherein said oligomerization is carried out at a temperature within a range of about 0° to about 250° C. and a pressure within a range of about atmospheric to about 2500 psig.

14. A process according to claim 12 wherein said inorganic oxide is selected from the group consisting of silica, silica-alumina, alumina, fluorided alumina, silated alumina, thoria, aluminophosphate, aluminum phosphate, phosphated silica, phosphated alumina, silica-titania, coprecipitated silica/titania, fluorided/silated alumina, and mixtures thereof.

15. A process according to claim 14 wherein said inorganic oxide is aluminophosphate.

16. A process according to claim 12 wherein said metal alkyl is a alkyl aluminum compound.

17. A process according to claim 16 wherein said alkyl aluminum compound is triethyl aluminum.

18. A process according to claim 12 wherein said unsaturated hydrocarbon is an aromatic hydrocarbon having less than about 70 carbon atoms per molecule.

19. A process according to claim 12 wherein said pyrrolide compound is selected from the group consisting of pyrrole, derivatives of pyrrole, alkali metal pyrrolides, salts of alkali metal pyrrolides, and mixtures thereof.

20. A process according to claim 19 wherein said pyrrolide compound is selected from the group consisting of pyrrole, 2,5-dimethylpyrrole, and mixtures thereof.

* * * * *